US012622587B2

(12) United States Patent
Monpeurt et al.

(10) Patent No.: US 12,622,587 B2
(45) Date of Patent: May 12, 2026

(54) NON-INVASIVE SENSOR AND MEASURING METHOD

(71) Applicant: ECLYPIA, Grenoble (FR)

(72) Inventors: Cyrielle Monpeurt, Grenoble (FR); Alexandre Gallegos, Paris (FR); Romain Blanc, Grenoble (FR)

(73) Assignee: ECLYPIA, Grenoble (FR)

( * ) Notice: Subject to any disclaimer, the term of this patent is extended or adjusted under 35 U.S.C. 154(b) by 0 days.

(21) Appl. No.: 18/848,496

(22) PCT Filed: Mar. 17, 2023

(86) PCT No.: PCT/EP2023/056879
§ 371 (c)(1),
(2) Date: Sep. 18, 2024

(87) PCT Pub. No.: WO2023/175139
PCT Pub. Date: Sep. 21, 2023

(65) Prior Publication Data
US 2025/0204790 A1 Jun. 26, 2025

(30) Foreign Application Priority Data
Mar. 18, 2022 (EP) ..................................... 22163111

(51) Int. Cl.
*A61B 5/00* (2006.01)
(52) U.S. Cl.
CPC .................................. *A61B 5/0093* (2013.01)
(58) Field of Classification Search
CPC .................. G01N 21/27; G01N 21/274; A61B 2560/0223; A61B 5/0093; A61B 5/0095;
(Continued)

(56) References Cited

U.S. PATENT DOCUMENTS

| 7,333,841 B2 | 2/2008 | Maruo et al. |
| 9,924,894 B2 | 3/2018 | Zhang et al. |

(Continued)

FOREIGN PATENT DOCUMENTS

| EP | 2460470 A1 | 6/2012 |
| WO | WO2019170716 A1 | 9/2019 |

(Continued)

OTHER PUBLICATIONS

International Search Report dated Apr. 20, 2023 for International Application No. PCT/EP2023/056879.
(Continued)

*Primary Examiner* — Amelie R Davis

(57) ABSTRACT

Method for measuring a parameter of interest in a target environment (2) by means of a non-invasive sensor (1) based on photoacoustic detection or photothermal detection, comprises: a) a sensor that comprises an adaptation module (14) is provided comprising a processor that implements an inverse modelling algorithm; b) the adaptation module chooses an initial model irradiation configuration; c) it determines, in a correspondence table, the optimal irradiation case; d) a light source irradiates the target environment according to the optimal irradiation case; e) a detection cell detects a signal; f) the processor of the adaptation module returns a current model configuration (CMmes) and an estimated value for the parameter of interest (Pest); g) the processor of the adaptation module evaluates the chosen model irradiation configuration, and only if this irradiation model configuration differs from the current model configuration; g1) it receives the current model configuration (CMmes).

7 Claims, 11 Drawing Sheets

(58) Field of Classification Search
CPC . A61B 5/14532; A61B 5/1455; A61B 5/7264;
A61B 5/7267
See application file for complete search history.

(56) References Cited

U.S. PATENT DOCUMENTS

| | | | |
|---|---|---|---|
| 10,888,242 | B2 | 1/2021 | Leabman |
| 2003/0023152 | A1 | 1/2003 | Abbink et al. |
| 2017/0042428 | A1 | 2/2017 | Kellnberger et al. |
| 2018/0333107 | A1 | 11/2018 | García Sada et al. |
| 2021/0247304 | A1 | 8/2021 | Jos et al. |

FOREIGN PATENT DOCUMENTS

| | | | |
|---|---|---|---|
| WO | WO2020086994 | A1 | 4/2020 |
| WO | WO2021212140 | A1 | 10/2021 |

OTHER PUBLICATIONS

Hu et al.."Generalized theory of the photoacoustic effect in a multilayer material" Journal of Applied Physics, Oct. 1, 1999, pp. 3953-3958, vol. 86 No. 7.
Tronstad Christian et al: "Non-invasive prediction of blood glucose trends during hypoglycemia", Analytica Chimica Acta, Dec. 15, 2018 pp. 37-48, vol. 1052, ISSN: 0003-2670, DOI: 10.1016/J.ACA.2018.12.009.
Rosencwaig, A et al. "Theory of the photoacoustic effect with solids", Journal of Applied Physics, 47, 64, 1976.

NON-INVASIVE SENSOR AND MEASURING METHOD

CROSS-REFERENCE TO RELATED APPLICATION

This application is a national stage application, filed under 35 U.S.C. § 371, of International Patent Application No. PCT/EP2023/056879, filed on Mar. 17, 2023, which claims the priority to European application No. 22163111.2 filed Mar. 18, 2022, the contents of which are incorporated by reference.

FIELD OF THE INVENTION

The present invention relates to a process measurement and a non-invasive sensor making it possible to measure one or more parameters of interest in a target environment.

More precisely, the invention relates to a non-invasive sensor based on the detection of a photothermal effect or photoacoustic, in particular configured to measure parameters in a target environment, such a stratified and/or evolving environment. A measured parameter can for example be blood sugar in the skin.

TECHNOLOGY BACKGROUND

In the field of sensors for living organisms, it is known to realize non-invasive sensors based on photoacoustic or photothermal detection.

A zone of interest of an environment to be analyzed, called target, is irradiated by means of a laser beam of chosen wavelength and modulation frequency depending on the parameter of interest to be measured. The laser beam is absorbed by the target over a depth which depends on the structuring of the target. Energy absorption light causes local heating of the target. In reaction to this heating, a thermal wave of frequency equal to the laser modulation frequency is generated in the target. This wave propagates in the target and in particular up to the exterior surface of the target.

The thermal wave can be directly detected and analyzed. We then speak of photothermy. Photoacoustics detection exploits the fact that the thermal wave is associated with a pressure wave frequency identical to the modulation frequency.

In the case of photoacoustic detection indirect, we detect the pressure wave generated in the fluid external environment when the thermal wave generated in the target reaches, after propagation, the interface target—fluid external environment.

This photoacoustic effect has been the subject of numerous theoretical studies. Allan Rosencwaig and Allen Gersho have notably developed a theoretical model of the photoacoustic signal. This model involves the physico-chemical properties of the sample to be analyzed, including the optical diffusion length, the thickness and the thermal diffusion length of the sample. (Rosencwaig, A. and Gersho, A. (1976), Theory of the photoacoustic effect with solids, Journal of Applied Physics, 47, 64).

Hu et al. have developed a theory generalized photoacoustic effect in a stratified material. (Hu, H., Wang, X., & Xu, X. (1999). Generalized theory of the photoacoustic effect in a multilayer material. Journal of Applied Physics, 86, 3953-3958.)

Photoacoustic detection presents many advantages compared to other techniques of detection among which we can cite the orthogonal aspect of transduction: the optical signal at the input of the environment to be analyzed is converted into an acoustic signal which is very specific to the phenomenon to be observed and which allows the use of inexpensive and miniaturized sensors.

The difficulty of photoacoustic detection or photothermal comes among others:

the number of parameters generally influencing the detected signal and, for certain analytes of interest present in concentration weak in the environment to be analyzed, of the weak proportion of the detected signal specific to each of these parameters of interest.

In a stratified material, to be able to deduce of the photoacoustic or photothermal signal the concentration of a given layer into an analyte of interest, it is therefore necessary to know all the other parameters influencing this signal. In particular, it is necessary to know the structure of the material, that is to say the thicknesses of the different layers constituting the material, their physico-chemical compositions (at the exception of the parameter of interest to be measured), as well that possibly their thermal conductivities or even the thermal resistance associated with each interface between two successive layers.

Calibration once and for all (or at all less for a significant duration of use) of a sensor based on photoacoustic or photothermal detection is only possible if only the parameter of interest varies in the target. On the other hand, when the characteristics of the stratified environment to be analyzed vary, it is necessary to calibrate the sensor regularly to obtain a measurement with acceptable precision. This problem arises more particularly for sensors intended for use on living organisms. For example, in the case of a non-invasive sensor of interstitial blood glucose monitoring, calibration of a non-invasive sensor based on photoacoustic detection or photothermal can only be obtained with a limited accuracy because the composition of the skin varies not only from one patient to another but also during the time for a given patient.

Document EP2460470 describes a process for regular calibration for a non-invasive blood glucose sensor including a close infrared laser source. We note that this sensor uses a method of detection other than photoacoustic or photothermal detection, since it is the fraction of the light wave incident which is transmitted or diffused by the material which is detected. Technical constraints and limitations of such a sensor, particularly in terms of consumption energy and measurement precision, are therefore not the same as those of a sensor based on photoacoustic or photothermal detection.

In the calibration process of EP2460470, a plurality of calibration models or a plurality of datasets to create these models, possibly obtained by numerical simulation, are stored in sensor memory.

At the time of calibration, an optical spectrum of the tissue to be analyzed, called the reference spectrum, is measured by irradiation of the tissue over a range of lengths of predetermined wave, on the basis of which a model of calibration is chosen for the measurements to be followed.

At a later analysis date, the optical spectrum of the tissue to be analyzed is measured again and a difference between the measured spectrum and the reference spectrum is calculated. The quality of the calibration model previously chosen is evaluated on the basis of this difference and if this assessment is unfavorable, a new calibration model is chosen to determine the blood sugar value measured. Blood sugar value is then determined by the sensor by substituting the absorbances measured at each wavelength of the spectrum in the calibration model.

Adapting the calibration model gradually over time following the process of EP2460470 allows to measure blood sugar with greater precision compared to blood glucose sensors whose calibration is done only once when adapting the sensor to the patient. The disadvantage of the process of EP2460470 is that it requires for each recalibration the acquisition of an optical spectrum of the tissue to be analyzed on a full range of wavelengths. This acquisition is associated with significant energy consumption.

Consequently, if we adapt purely and simply the method of EP2460470 with a continuous sensor based on indirect photoacoustic detection, the energy cost of this process is not sustainable or requires a battery whose weight is difficult to accept for a patient who would be equipped with such a sensor.

Furthermore, photoacoustic detection requires not only a choice of wavelength but also a choice of laser modulation frequency. Indeed, the depth of penetration of the laser into the target depends on the modulation frequency of the laser. If the structure of the target (e.g. skin) changes over time, the modulation frequency at use to measure the parameter of interest (e.g. interstitial blood glucose) also changes over the time. To implement the calibration process of EP2460470 on a sensor based on photoacoustic detection or photothermal, it would therefore be necessary not only to vary the wavelength of the laser as before to be able to calculate the difference between the reference spectrum and the calibrated spectrum but also the modulation frequency of the laser. In in other words, it would be necessary to obtain before each measurement (or each measurement series) series of optical spectra of the target at varying modulation frequencies. The energy consumption problem would be therefore further increased if we carried out a simple transposition of the method of EP2460470 to a non-invasive sensor based on indirect photoacoustic detection.

Finally, EP2460470 poses a skin model a priori, composed of three layers: a surface layer of 0.1 mm thick, an internal layer of 0.9 mm thick and a subcutaneous layer of 2.0 mm thickness. Even if EP2460470 mentions the possibility (in § 79) to use the (overall) thickness of the skin as a variable in the simulations, it neither prove of the feasibility of such an embodiment nor does it indicate if it is possible to take into account a number of layers different from three. The calibration process of EP2460470 therefore does not seem capable of taking into account all the variability intrinsic to the stratified environment to be studied. The invention therefore aims to improve the precision of a non-invasive sensor in a target environment, in particular stratified and/or scalable based on photoacoustic or photothermal detection while controlling energy consumption of this sensor or to reduce consumption energy of this sensor while controlling its precision.

SUMMARY OF THE INVENTION

Thus, the invention relates to a method of measurement of a parameter of interest in a target environment means of a non-invasive sensor based on the photoacoustic detection or photothermal detection, including:
a) we provide a sensor comprising:
   a light source,
   a device for controlling irradiation parameters from the light source,
   a detection cell configured to detect an acoustic or thermal signal,
   a memory in which a is stored correspondence table including model configurations each representative of a given state of the target environment and irradiation optimal cases each comprising a set of parameters irradiation, each model configuration being associated with an optimal irradiation case,
and an adaptation module exchanging information with the detection cell and the device for controlling irradiation parameters of the light source, the adaptation module comprising a processor adapted to implement an inverse modeling algorithm receiving as input a case of irradiation comprising a set of irradiation parameters and a signal acoustic or thermal and providing on the output a model configuration and a value of the parameter of interest;
b) the adaptation module chooses an initial irradiation model configuration;
c) the adaptation module determines in the correspondence table the optimal irradiation case for the chosen irradiation model configuration; i.e. the irradiation case that allows the parameter of interest to be measured with a pre-determined accuracy and/or the amount of measurement data that allows the lowest energy consumption.
d) the light source irradiates the target environment following the set of irradiation parameters of said optimal irradiation case;
e) the detection cell detects an acoustic or thermal signal generated in response to irradiation;
f) the processor of the adaptation module implements the inverse modeling algorithm, receives as input the acoustic or thermal signal detected by the detection cell and the optimal irradiation case used for irradiation, and returns on the output a current model configuration and a value of the interest parameter estimated;
g) the processor of the adaptation module evaluates the irradiation model configuration chosen by comparison with the current model configuration, and only if this evaluation is unfavorable: g1) the adaptation module (14) receives as input the current model configuration (CMmes) and returns release a new model configuration in sight of irradiation (CMirrad), then we repeat c), d), e) and f);
h) the value of the parameter of interest measured (Pmes) by the sensor is the last value of the parameter of interest estimated (Pest).
Thanks to these provisions, it is possible to obtain a blood sugar measurement with:
either a single irradiation (no execution of the sub-step g1, in the case of a favorable evaluation). This irradiation is then carried out according to an irradiation case chosen by default but corresponding to a controlled energy consumption (the parameters of irradiation being for example chosen in limited number). Step g) of evaluating the irradiation model configuration makes possible to acquire the certainty that the precision of the measurement was indeed the highest possible for the present case in view of the cases of irradiation available in the correspondence table, which is therefore an advantage compared to a process in which step g) is not provided and for which we do not have this certainty;
either two irradiations (step g with execution of the sub-step g1, in the case of an unfavorable evaluation) and therefore including a reiteration of c), d), e) and f)). The second irradiation is then carried out depending on the case of irradiation allowing the precision to be obtained the highest possible for the specific case in view of the additional information acquired thanks to the first irradiation and cases of irradiation available in the correspondence table. The precision of the process is therefore known and improved compared to a process not having step g).

The method therefore allows in the first case a validation of the chosen irradiation parameters and to acquire the certainty that the precision of the measurement is the best possible for this sensor configuration and the state of the target on the date of the measurement taking into account the additional information acquired during irradiation, and in the second case, an adaptation of the parameters of irradiation to obtain in a second step the best possible measurement accuracy taking into account the additional information acquired during the first irradiation, all being carried out with a consumption controlled energy and in particular without requiring the acquisition of complete or frequency spectra irradiation or modulation frequency. We note that the correspondence table is essential for this process. It is this correspondence table which allows to associate with each current model configuration or chosen for irradiation the most suitable case of irradiation and therefore limit energy consumption for each irradiation.

According to different aspects, it is possible to predict one and/or the other of the characteristics below taken alone or in combination.

According to one embodiment, g1) includes we reiterate g) after f). In this case, the irradiation is repeated as long as the irradiation parameters used are not the optimal irradiation parameters for the state of the target on the measurement date, and optionally as long as the number of repetitions is below a predetermined threshold value.

This embodiment allows, in particular if the repetition of the irradiation is done at a higher frequency at the characteristic frequency of modifications of the structure of the target, to converge gradually close to the irradiation parameters making possible to obtain the best precision. Once again, consumption energy for each irradiation being controlled due to the fact that the number of irradiation parameters is limited for each case of irradiation, even if the convergence is only obtained after three, four, five or even ten successive irradiations, energy consumption overall can be controlled and in particular less than that which would be necessary for the acquisition of a complete spectrum in irradiation frequency at/or in frequency of modulation, while controlling or even improving simultaneously the measurement accuracy.

According to one embodiment of the process, we generate beforehand a correspondence table using a processor and a database model configuration including bytes (configuration model, case of irradiation, parameter of interest) and an acoustic or thermal signal detected by the cell detection associated with each byte and we store this correspondence table in the memory of the non-invasive sensor.

Thanks to this arrangement, the correspondence table is obtained in an automated manner and can by example be updated when the database model configurations are enriched or must be adapted to a given patient or type of patient.

According to one embodiment, the method of measurement includes:

a processor learns at least one modeling algorithm reverse from database model configurations and we store at least one inverse modeling algorithm in the memory of the non-invasive sensor.

Thanks to this arrangement, one or more inverse modeling algorithms can be learned from automated way, for example each adapted to a model configuration and a given irradiation case or a group of model configurations and given irradiation cases. According to one embodiment of the method, at least part of the acoustic or thermal signals detected by the detection cell associated with bytes stored in the database model configurations are simulated, that's to say, they are generated using a computerized simulation device.

Thanks to this arrangement, it is possible to generate a large number of bytes, for example corresponding to states of the target environment as varied as possible and to irradiation cases, also as varied as possible, much faster and less costly than if these bytes were obtained by experiment in real situation. In the case where the target environment is a tissue of a living being, such as skin, it is possible to generate bytes corresponding to rare physiological situations, extreme or simply more varied than those that would be accessible with a set of test patients. A generated correspondence table from such a database can therefore cover a much wider range of situations with a much finer grain than in the absence simulation, which ultimately allows the generation of optimal irradiation cases better adapted in terms of consumption and/or precision for each configuration model.

The invention further relates to a non-invasive sensor based on photoacoustic or photothermal detection configured to measure a parameter of interest in a target environment comprising:

a source of light, a device for controlling irradiation parameters from the light source, a detection cell configured to detect an acoustic or thermal signal, a memory in which a correspondence table including model configurations each representative of a given state of the target environment and optimal irradiation cases including each a set of irradiation parameters, each model configuration being associated with an optimal irradiation case, the non-invasive sensor further comprising an adaptation module adapted to exchange information with the detection cell and the device for controlling the irradiation parameters of the source of light, the adaptation module comprising a processor suitable for implementing an inverse modeling algorithm receiving as input an irradiation case including a set of irradiation parameters and an acoustic or thermal signal and providing output a model configuration and a value of the parameter of interest, the adaptation module being further configured for:

i—choose an initial irradiation model configuration, ii—determine in the correspondence table an optimal irradiation case corresponding to an irradiation model configuration, iii—transmit an optimal irradiation case to the device for controlling irradiation parameters from the light source, iv—receive a signal detected by the detection cell, v—determine a current model configuration and a value of the parameter of interest estimated on the basis of a photoacoustic or photothermal signal detected received and an optimal irradiation case, vi—evaluate an irradiation model configuration compared to a model configuration in progress, vii—only if the irradiation model configuration of the chosen target stratified environment and the model configuration of the current target stratified environment being compared are different, determine a new irradiation model configuration when it receives a current model configuration, determine a new optimum irradiation case from the correspondence table, corresponding to the new irradiation model configuration, and transmit the new optimum irradiation case to the irradiation parameter control device, so that the light source irradiates the target stratified environment according to the irradiation parameter set of the new optimum irradiation case, and the detection cell detects a new thermal or acoustic signal generated in response to this irradiation, and transmits it to the irradiation parameter control device. the target stratified environment according to the set of irradiation parameters of the new optimal irradiation case, and that the detection cell detects a new thermal or acoustic signal generated in response to this irradiation and transmits it to the processor of the adaptation module (14) configured to reiterate Iv, v, vi and vii;

viii—determine the value of the parameter of interest measured based on the last value of parameter of interest estimated.

Thanks to this arrangement, the sensor can measure with controlled precision and/or consumption a parameter of interest in a target environment, in particular a tissue of a living being. The invention concerns finally a computer program including instructions which drive the non-invasive sensor following the previous embodiment to execute the steps of process according to any one of the embodiments described above.

BRIEF DESCRIPTION OF THE DRAWINGS

Embodiments of the invention will be described below with reference to the drawings, described briefly below:

FIGS. 6a, 6b and 6c represent the results of an influence analysis of the variables of type SHAP ("SHapley Additive explanations") carried out on three inverse models trained respectively on:

FIG. 6a: a first "thick stratum" group, which corresponds to model configurations of bilayer skin in which the thickness of the upper layer, modeling the stratum corneum, is greater than 18 μm;

FIG. 6b: a second "thin stratum" group which corresponds to model configurations of bilayer skin in which the thickness of the upper layer, modeling the stratum corneum, is less than 18 μm;

FIG. 6c the whole of the first and the second band;
each of these models being trained from the signals detected following irradiation at six different modulation frequencies.

In FIGS. 6a, 6b and 6c, the abscissa axis represents the SHAP value. Each point of a figure corresponds to a Shapley value for a variable and one instance. The position on the vertical axis is determined by the variable and on the abscissa axis by the Shapley value. The intensity (in shades of gray) color represents the value of the variable.

FIG. 7b shows the predicted blood glucose value by a second inverse model, trained on the first "thick stratum" group from signals detected following irradiation according to the two variables the most influential for this group, identified in FIG. 6a.

Figure 1:
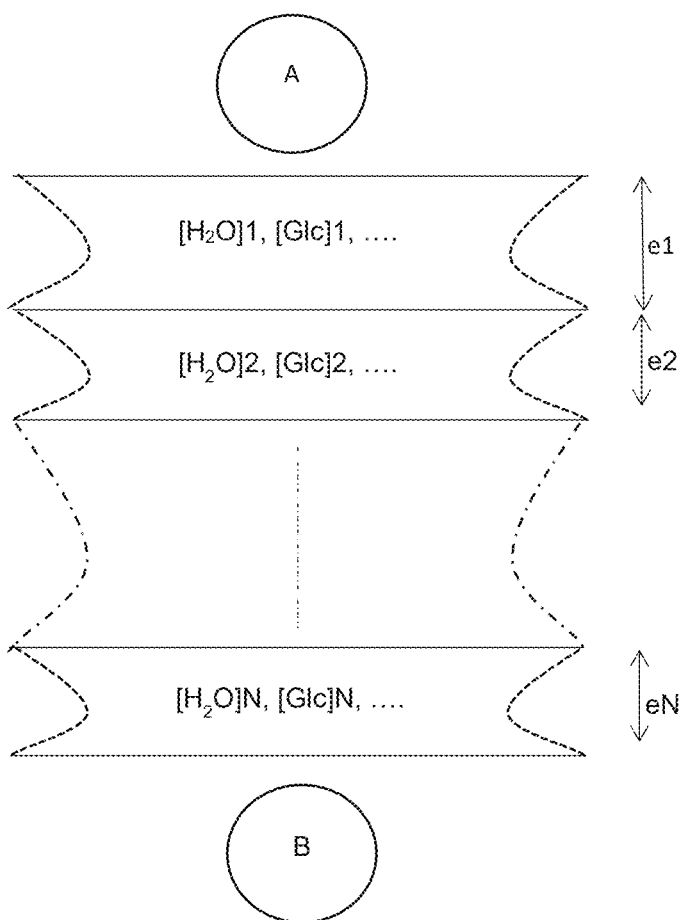
FIG. 1 represents a typical modeling of a skin-like stratified target environment.

In the drawings, identical references designate identical or similar objects.

DETAILED DESCRIPTION

The invention relates to a non-invasive sensor 1 of one or more parameters of a target environment 2, in particular of a stratified target environment 2 whose structuring can possibly evolve over time. The stratified target environment 2 can be, for example, a fabric of a human or animal organism, such as the skin.

The parameters to be measured are called in the following "parameters of interest".

A parameter of interest may in particular be a physiological parameter in the case where the stratified environment is a tissue from a human or animal.

For example, the physiological parameter to be measured is blood sugar, especially interstitial blood sugar. It could also be a matter of measuring the water content in a particular layer of the skin or even the lactate concentration of a particular layer. These Examples are not limiting.

Sensor 1 can be wearable and it can allow continuous monitoring of the parameter(s) of interest.

The non-invasive sensor 1 can be based on the photoacoustic detection or photothermal detection.

The measurement method is particularly suitable for improving the accuracy of a non-invasive sensor based on indirect photoacoustic detection, for which the sensor detects an acoustic wave generated in a fluid environment, in particular a gas, surrounding the target environment 2 in response to irradiation, while controlling its consumption energy or to reduce consumption energy of the sensor while controlling its precision. However, it is entirely possible to implement this process on a non-invasive sensor based on photothermal energy or direct photoacoustic detection to obtain one of the two technical effects previous ones. To simplify understanding, the example indirect photoacoustic detection will be described more in detail below, but the generalization to a sensor based on indirect photoacoustic or photothermal energy will be done without difficulty.

Figure 3:
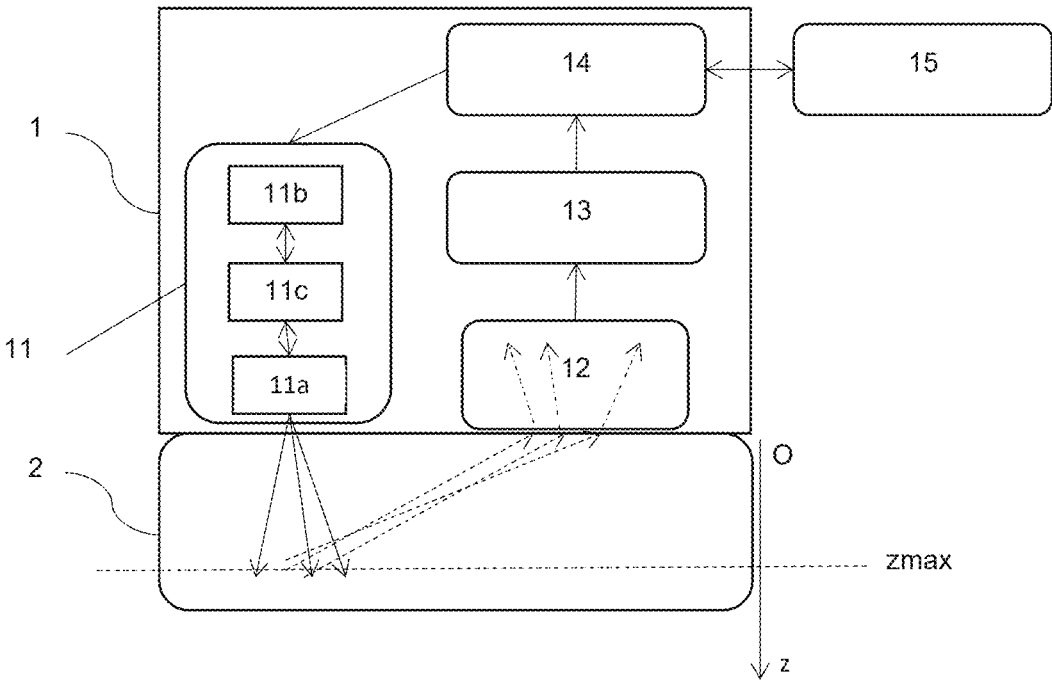
FIG. 3 shows the main elements of a sensor 1 according to the invention, the sensor 1 being in this case positioned in contact with the target environment 2.

The non-invasive sensor 1 is represented schematically in FIG. 3. It includes:

an irradiation device 11 comprising a light source 11a, an intensity modulation device of this light source 11b, a control device 11c of at least one modulation frequency to which the intensity modulation device 11b modulates the intensity of emitted light by the light source;

at least one photoacoustic detection cell 12 detecting a signal generated in response to irradiation of a target environment 2 by the light emitted, for example detecting directly or indirectly a thermal wave which propagates in a target environment 2;

a signal processing module 13 configured to receive and process data from at least one detection cell 12;

an adaptation module 14 of the irradiation parameters and the calibration model;

a simulation module 15, remote or on-board with the other elements of the non-invasive sensor 1.

In a particular embodiment, the light source 11a emits a laser beam modulated in intensity at at least one particular wavelength towards the target environment 2.

The light source 11a can in particular be a light-emitting diode (LED), or a laser chip. The light source 11a can, in addition or alternatively, understand a quantum cascade laser (QCL) emitting in the mid-infrared region (MIR-QCL), a ICL laser ("interband cavity laser", a cavity laser internal or external, a GaSb laser. These examples are not limiting. The light source 11a can be chosen depending on the target environment 2 and/or the parameters of interest.

The non-invasive sensor 1 may include several light sources 11a.

The non-invasive sensor 1 also includes the circuits associated with the light source(s) 11a and at least one control device 11c configured to control the irradiation parameters of the light source (11a) in particular:

the frequency with which at least one device intensity modulation 11b modulates the intensity of at least one light source 11a, so that the intensity of the light emitted by the light source 11a is modulated at an adjustable modulation frequency.

and optionally, the wavenumber (or equivalently the wavelength) of a light emitted by the light source 11a and/or optionally the luminous power of light source 11a at a given wavelength.

Frequency modulating the intensity of a given light source 11a at a given wavelength is called f mod ($\lambda$) in the rest of the description.

Several wavelengths can be associated with the same modulation frequency, and several modulation frequencies can be associated with the same wavelength. The light emitted by a light source 11a at a given wavelength $\lambda$ can be characterized by this wavelength and the corresponding modulation frequency and optionally the corresponding light power and/or other parameters such as integration time or duty cycle characterizing the laser pulses.

The light source 11a can be modulated in intensity by any known electrical or mechanical means.

The light can be emitted by a light source 11a given continuously or pulsed.

The incident light on the target environment 2, emitted by the light source(s) 11a modulated in intensity, propagates to target environment 2 then through this target environment 2 (phenomenon symbolized by arrows in solid lines in FIG. 3).

It is then gradually absorbed by the different constituents of this target 2, on a depth zmax which depends on the structure of the target environment 2 and its physicochemical composition. The absorption of light energy causes a local heating of the target environment 2. Consequently, a thermal wave of frequency equal to the frequency modulation of the light source propagates in the target environment 2 (phenomenon symbolized by arrows in dotted lines in FIG. 3), particularly towards the surface of the target environment 2. This thermal wave gives rise in the gaseous environment outside the target at a pressure wave of the same frequency, which propagates in this gaseous environment surrounding the target environment 2 and in particular in the photoacoustic detection cell 12 (phenomenon symbolized by dotted arrows alternated in FIG. 3).

The detection cell 12 includes in the case of photoacoustic detection a filled chamber of a gas (for example air) through which propagates the acoustic wave, and one or more sensors appropriate placed in this room, for example facing in the target environment 2. This is for example one or more electroacoustic sensors configured to convert the pressure of the acoustic wave into an electrical signal, such as a microphone or a piezoelectric transducer.

Each electroacoustic sensor is functionally connected to the signal processing module 13.

The signal processing module 13 may include a configured analog-to-digital converter to convert the analog electrical signal from electroacoustic sensor into a digital signal.

The signal processing module 13 may include a synchronous detection device suitable for demodulate and extract the signal of interest from the detected signal.

The signal processing module 13 comprises possibly an operational amplifier connected operationally to the analog-to-digital converter and configured to amplify the electronic signal derived from the acoustic response of target 2 transmitted by an electroacoustic sensor.

In example embodiments, the analog-to-digital converter is functionally connected to a digital signal processor for digital signal processing.

The non-invasive sensor 1 according to the invention comprises in addition a parameter adaptation module 14 of irradiation and the calibration model, as well as a simulation module 15. These two elements are described in the following sections.

Adaptation Module 14

The adaptation module 14 is a computerized device comprising at least one processor which can exchange information with the simulation module 15 described below;

which can receive information from the cell detection 12 and/or the signal processing module 13 if applicable;

and which can transmit information to the control device (s) 11c of at least one irradiation parameter of the light source 11a (for example a modulation frequency at which the device intensity modulation 11b modulates the intensity of light emitted by the light source 11a at a given wavelength, the wave number (or equivalently the wavelength) of light emitted by the light source 11a, the light power of the light source 11a at a given wavelength and optionally a given modulation frequency, . . . ).

Figure 2:
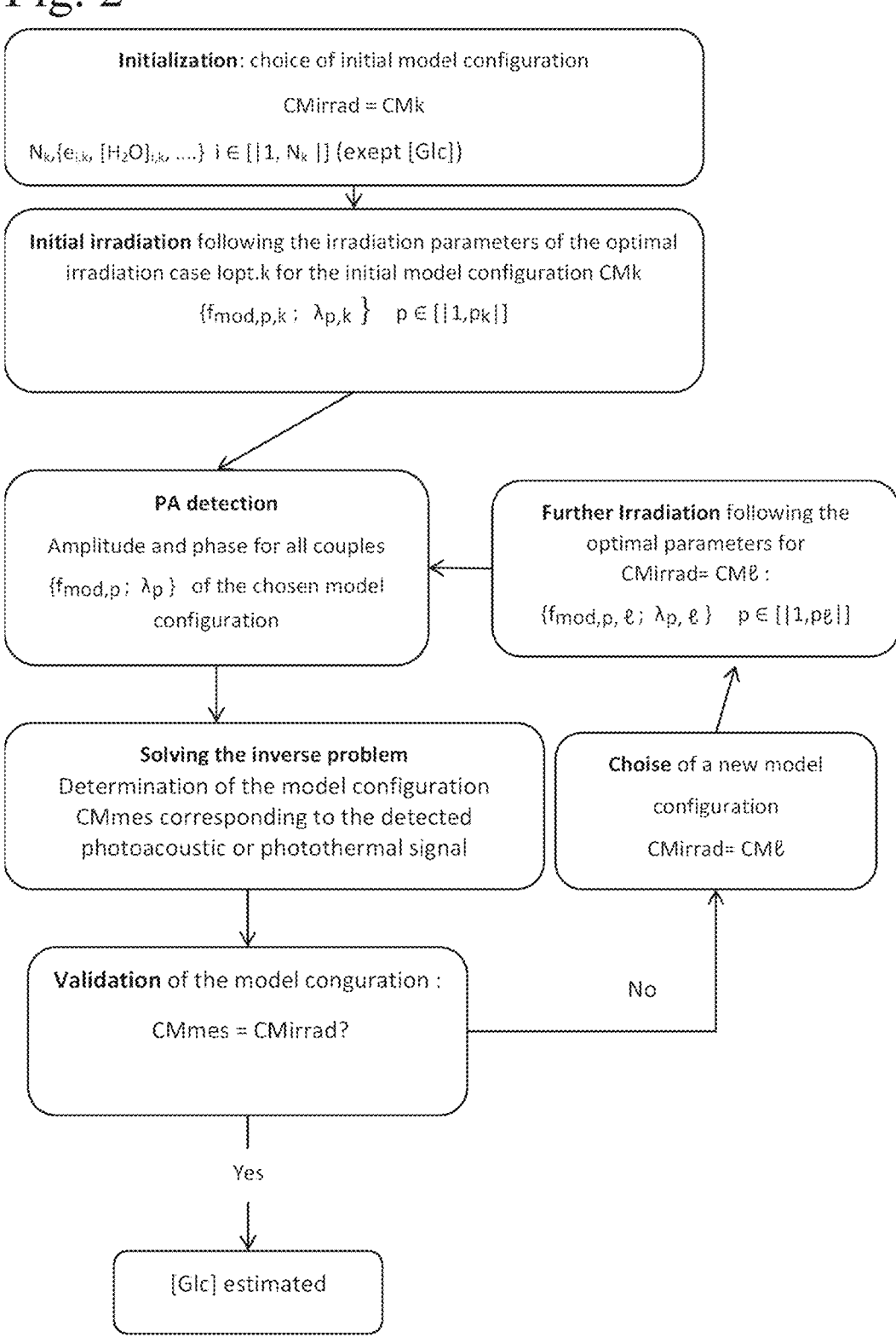
FIG. 2 represents the steps of a process of optimized measurement in a particular embodiment of the invention, in the case where one wishes to measure a patient's interstitial blood glucose.

The steps implemented by a non-invasive sensor 1 comprising an adaptation module 14 for a measurement of the parameter of interest are represented schematically in FIG. 2 in the particular case where the target environment 2 is the skin (in this case it is therefore of a stratified environment)

and the parameter of interest is blood glucose interstitial.

The non-invasive sensor 1 further comprises a storage memory for a configuration database models, a correspondence table and of one or more inverse models which are described below.

This storage memory can be distributed and/or shared in/with the adaptation module (14) and/or the simulation module (15).

The adaptation module 14 carries out the steps of the process which allow to choose, in the configuration database models, the model configuration of target environment 2 most adapted to the target environment 2 to the date of the measurement, to choose, based on the correspondence table, the optimal irradiation parameters for measurement and determine the inverse model the most suitable, that is to say the most precise, for the calculation of parameter measured from the signal detected for this special measure. We will describe these steps after having described the steps allowing to generate the database model configuration and the correspondence table.

The model configuration database and the correspondence table are generated from a simulation module 15, embedded in sensor 1 or distant. In the case where the simulation module 15 is remote, the non-invasive sensor 1 comprises means of communication so that the simulation module 15 and the adaptation module 14 exchange data.
Simulation Module 15

Figure 4:
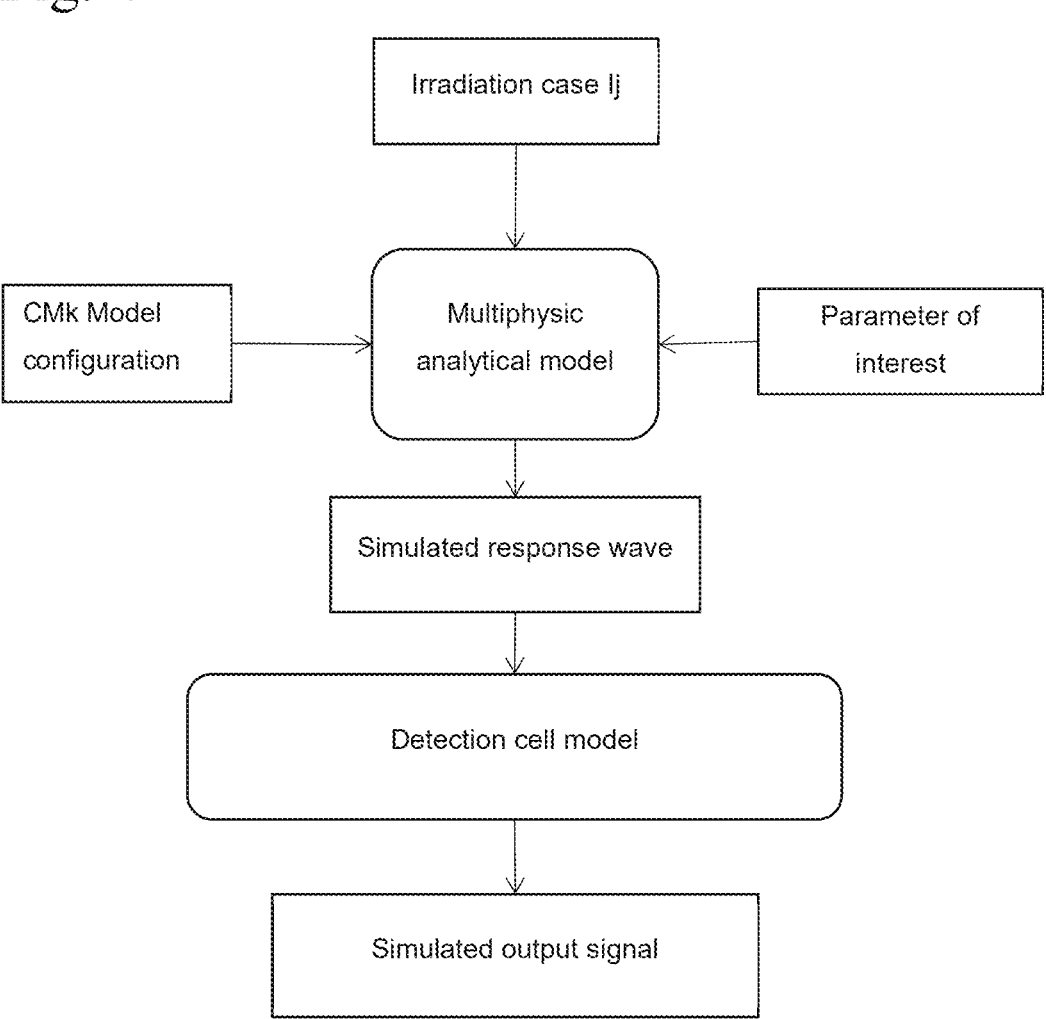
FIG. 4 represents the steps implemented by the simulation module 15 to simulate a photoacoustic signal that would be detected by a photoacoustic cell given in response to irradiation of a target stratified environment modeled using the parameters of the CMk model configuration following the irradiation parameters of the irradiation case Ij.

The simulation module 15 is a computerized device configured to generate a set of configurations corresponding models (or even modeling or describing) each to a particular state of the target environment 2, a set of irradiation cases of the target environment 2 and photoacoustic (or, where applicable, photothermal) signals theoretically detected in response to each irradiation case for each model configuration CMk of the target environment 2 from analytical models of the target environment 2 and the photoacoustic detection cell (or where applicable photothermal) 12, as shown in FIG. 4.

This simulation module 15 is particularly relevant in the case where the target environment 2 is evolving over time and/or stratified. In this case, the target environment 2 adopts real configurations over time different (because one or more concentrations vary within one or more layers of the target environment 2, one or several dimensions such as, for example, thickness one of the layers of the target environment 2 and/or the number of layers in the target environment 2 varies) which can each be modeled by a model configuration particular.
a) Multiphysics Analytical Model of the Target Environment 2

The target environment 2 to be analyzed is modeled as shown in FIG. 1. The target environment 2 separates an exterior environment A of an interior environment B and is composed of a succession of N layers whose interfaces are for example assumed to be locally plane. Each layer i (i∈[[1, N]]) is described by the parameter(s) of interest and a number of explicit parameters (called level 1 parameters because their values will be provided as input to the simulation module 15 for each simulation) appropriate for the target environment 2 considered. For example, if target environment 2 is the skin and that we seek to measure a glucose concentration in a layer j of this target environment 2, the target environment 2 will be described by its number of layers N, the concentration [Glc]j of interest, and each layer i can be described for modeling by its thickness ei, its concentration in water [H2O]i. We can possibly take into account glucose concentrations [Glc]i for i≠j. In this case the values of ei (i∈[[1, N]]), the concentrations [H2O]i (i∈[[1, N]]) and the [Glc]i concentrations for (i∈[[1, N]], i≠j) are the level 1 parameters.

The list of level 1 parameters can be enriched if we wish to carry out more precise modeling. In particular, the concentrations of other components of the skin such as fats, lactate, oxygen, etc., can be included in the list of level 1 parameter describing a layer of the skin.

Still for the example of the skin, we can consider taking into account skin color, the age of the patient, or any other anthropometric parameter, so as to expand or restrict the space of possible models.

Non-explicit parameters of the model target environment 2 (called level 2 parameters because no provided as input to the simulation module 15) can be calculated using analytical models. For example, thermal conductivity, heat capacity, the density or the absorption coefficient at each wavelength of each layer of the target environment 2 can be deduced from level 1 parameters and known equations.

Parameter(s) of interest playing a particular role, it is not included in the level 1 settings list. Depending on the stage of the process, this parameter of interest will be known or not: its value is known to carry out the simulations using simulation module 15, but it is of course unknown in the case of a real measurement with the non-invasive sensor 1.

The number of layers N of the target environment 2 can also be a variable in the model. Still in the example of the skin, depending on physiological situations, N can thus be greater than or equal to one or two. So, for certain physiological situations, the skin may be correctly described by two layers, the first corresponding to the stratum corneum, the concentration of which in glucose can for example be low, and the second to the rest of the skin, the glucose concentration of the second layer being assimilated to the concentration of interstitial glucose to be measured.

For other situations, a three-layer model or more will be more suitable. In the latter case, the water concentration of a layer could for example increase with the depth at which this layer is located.

The number of layers N of the target environment 2 may therefore not be a constant.

In the case of the skin, the external environment A is in general the atmosphere surrounding the patient, which fills also the photoacoustic detection cell.

The simulation module 15 implements a multiphysic analytical model of stratified environment 2 based for example on physical and/or chemical equations such as, by way of non-limiting example, the equations of Beer-Lambert for optical absorption and thermodynamic equations of heat (Fourier's law and conservation laws).

A CMk model configuration (k positive integer) of target environment 2 corresponds to (or even modeled) a particular state of the given target environment 2. This particular state is assumed to be correctly represented by the data of number of layers N and values of the parameters level 1 for each layer.

For each CMk model configuration, the multiphysic analytical model allows, if the parameter of interest is more known, to simulate the thermal wave generation at the layer 1/external environment A interface (interface 1/A) in response to irradiation by a light source 11a whose irradiation parameters are known, i.e. for example, the wavelength λ, the modulation frequency f mod(λ) of this wavelength and the surface density of power of this wavelength.

As a variant, the multiphysic analytical model allows to simulate the pressure wave generated in the external environment A.

In both cases, the signal obtained at output of a processor implementing the multiphysic analytical model is called "simulated response wave"

The simulated response wave can be provided as input of a processor implementing the detection cell model.

b) Detection Cell Model

The non-invasive sensor 1 based on the photoacoustic detection or photothermal includes a photoacoustic detection cell (respectively phothermal) 12 configured to detect and analyze the wave pressure (respectively the thermal wave) generated in the external environment A when the thermal wave generated in target environment 2 in response to irradiation reaches interface 1/A.

The entire detection cell 12 can be modeled analytically. From a response wave simulated by the multiphysic analytical model, which would theoretically be received at the input of the detection cell 12, the detection cell model 12 allows to predict the output signal of the detection cell 12.

Different models can be considered.

Thus, in the case of indirect photoacoustic detection, the parameters of the detection cell model 12, called cell parameters in the following, can include these dimensions (for example the size of the vent, the height of the cell, etc.), parameters thermodynamic states (temperature, pressure atmospheric, relative or absolute humidity, etc.). The photoacoustic detection cell can in particular be modeled using an equivalent RLC circuit. For example, the model described in Dehe, Alfons et al. "Tea Infineon Silicon MEMS Microphone." (2013) may be suitable.

It is possible to include in this photoacoustic detection cell model a step model signal processing carried out by the processing module of signal 13 if necessary, so as to generate, from each simulated response wave generated by the processor which implements the multiphysic analytical model, the signal theoretically obtained at the output photoacoustic detection cell (and the case applicable after processing of the signal by the processing module of signal 13) which corresponds to it.

The processor of the simulation module 15 can be configured to implement the photoacoustic detection cell model of.

Thanks to the multiphysic analytical model of target environment 2 and the detection cell model 12, we therefore has a global analytical model that allows from the data of the CMk model configuration of target environment 2 and the irradiation case Ij, on condition of providing furthermore the parameter of interest (which can effectively be chosen since it is a simulation), predict the expected signal at the output of the detection cell 12 or, where applicable, the processing module of the signal 13. This is shown in FIG. 4.

In summary, the simulation module 15 receives therefore as input the parameters of the model configuration CMk of target environment 2, that is to say the number of N layers of target environment 2 and level parameters 1 for each layer, as well as the parameter of interest and the irradiation parameters of the irradiation case Ij, an irradiation case comprising one or more wavelengths of light emitted by one or more lasers, one or more frequencies of respective modulation of the intensity of said laser(s), and optionally the respective powers irradiated by said laser(s). In output, the simulation module 15 provides the signal theoretically expected at the output of the detection cell 12 or if necessary, the simulated signal theoretically processed expected at the output of the signal processing module 13 for the CMk model configuration of target environment 2 chosen, called simulated output signal.

The simulated output signal can be stored in memory in the form of a Fourier spectrum.

The bytes {CMk model configuration of target environment 2, irradiation case Ij, parameter of interest, amplitudes and phases of the components of the output signal simulated} can be stored in a database of model configurations.

Database of Model configurations

We can therefore generate, possibly in an automated manner and/or random, a large number of CMk model configurations, each model configuration CMk corresponding to a number of layers N and a set of level 1 parameters, and optionally a value or range of values of the parameter of interest, describing a particular situation in the target environment 2 of interest.

For each CMk model configuration, we can generate, possibly in an automated manner and/or random a large number of irradiation cases Ij, each irradiation case corresponding to a set of parameters of irradiation describing the parameters of the light source(s) 11a used for irradiation.

An irradiation case Ij can therefore include one or more intensity modulation frequencies of one or more lasers, the wavelength of each of these lasers and optionally the irradiated power by each laser.

Using the simulation module 15, we calculate the amplitude and phase of each component of the simulated output signal obtained at the processor output of the simulation module 15 implementing the global analytical model including in where applicable the multiphysic analytical model and sensing cell model for each CMk model configuration for each irradiation case Ij, a value of the parameter of interest being additionally provided.

The irradiation cases Ij can be the same for several different CMk model configurations, and possibly several values of the parameter of interest, or different from a CMk model configuration to another and/or a value of the parameter of interest to another. Once the simulations have been carried out, we can store in a database of configurations model all these CMk model configurations, irradiation cases, values of parameters of interest and photoacoustic signals (or where applicable photothermal) associated simulated as bytes {template configuration CMk, irradiation case Ij, parameter of interest, amplitude and phase of the components of the simulated output signal}

Generation of CMk model configurations and/or irradiation cases Ij may not be completely random.

Generation of CMk model configurations may, among other things, be based on physiological considerations to restrict the space of possibilities to physiologically realistic model configurations. For example, we can limit the possible thicknesses from the first layer of skin to the range [8 mm, 40 mm] which is actually observed experimentally, and limit the water concentrations of this layer to a restricted range for each thickness, the concentration in water of the stratum corneum being correlated with its thickness.

The generation of irradiation cases Ij can in particular take into account the limitations of light sources 11a available for a non-invasive sensor 1 given in wavelength and/or power, or even ranges of modulation frequencies relevant to the type of target environment 2 to analyze, or wavelengths relevant to the parameter(s) of interest.

As a variant, the configuration database models can only include bytes {CMk model configuration, irradiation case Ij, parameter of interest, amplitudes and phases of the components of the actually measured signal} obtained by experiments in real situations or include at the same time such bytes obtained in a real situation and bytes obtained by simulation.

Correspondence Table

From the database of model configuration, we can train in the simulation module 15 an artificial intelligence model.

Figure 5:
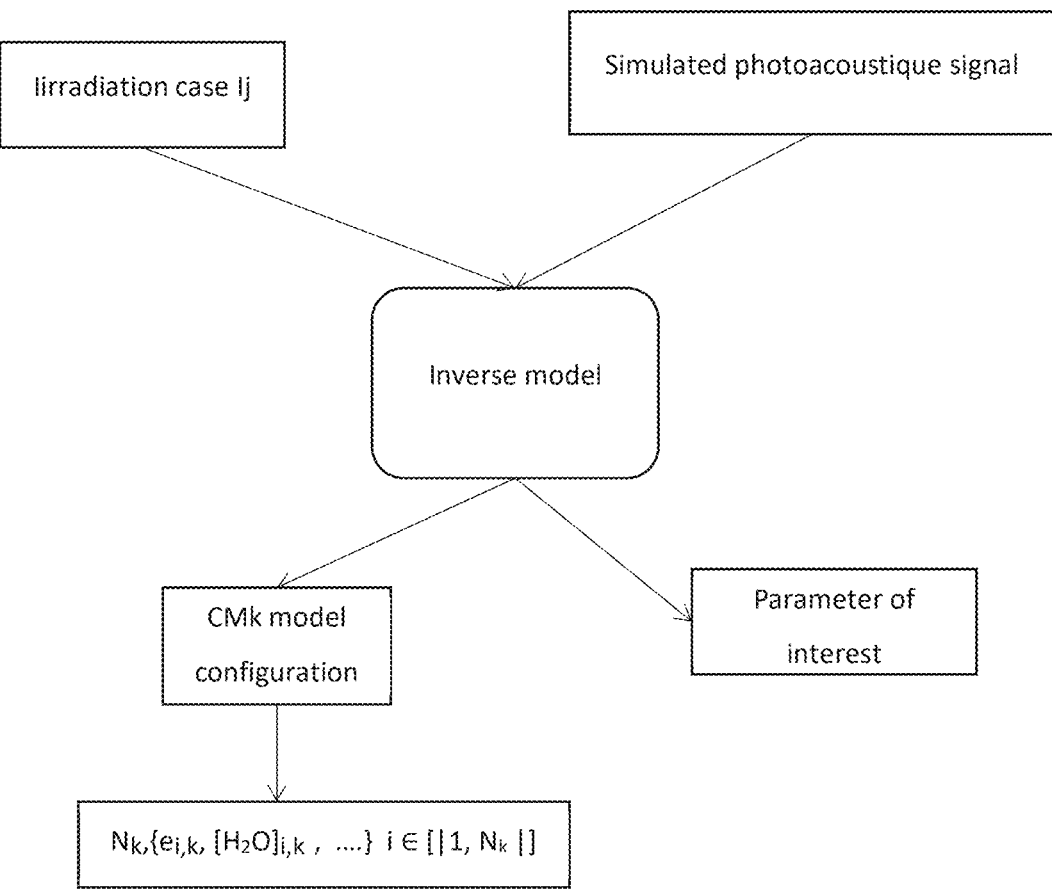
FIG. 5 shows how a model works reverse.

The artificial intelligence model, after learning, is able to solve the inverse problem, that is to say, to find the param- eter(s) of interest and the CMk model configuration of target environment 2, therefore the number of layers N and the level parameters 1, knowing the simulated photoacoustic signal and the irradiation parameters of the irradiation case Ij, such as shown in FIG. 5.

The learned model, which we will call the inverse model afterwards, can be transmitted to the adaptation module 14 and stored in the memory of this module.

Several different inverse models can be learned, with learning games and/or different learning rules.

To the extent that several irradiation cases Ij can be associated with the same CMk model configuration, it is also possible using statistical analysis techniques and/or artificial intelligence to identify the irradiation case Ij which makes possible to measure the parameter of interest with the desired precision and/or quantity of data measurement allowing the weakest energy consumption.

In particular, we can carry out an analysis of the influence of variables ("feature importance") in the trained model. At the end of this analysis, we can associate with each CMk model configuration an irradiation case I opt. k optimized, including a restricted irradiation wavelengths number and a restricted f mod modulation frequencies number for each irradiation wavelength.

It is possible to work model configuration by model configuration or to categorize the model configurations and associate with each category of model configurations an optimal irradiation case I opt. cat.k.

The interest of the correspondence table can be under-stood in the light of FIGS. 6a to 9b. The context of these figures is that of measuring interstitial blood glucose in the skin. Inverse models are trained on a database of model configurations including, in this context, bytes (configura-tion model (CMk), irradiation case (Ij), parameter of inter-est) and an acoustic or thermal signal detected by the detection cell associated with each byte.

The data from the database were segmented into two groups:

the first "thick stratum" group corresponds to bilayer skin model configurations in which the thickness of the upper layer, modeling the stratum corneum, is greater than 18 mm;

the second group "thin stratum" corresponds to bilayer skin model configurations in which the thickness of the upper layer, modeling the stratum corneum, is less than 18 mm.

An inverse model is trained for each group from signals detected for six different modulations frequencies. Then an analysis of the influence variables is carried out on each of the two inverses models obtained, as shown in the FIGS. 6a and 6b. This analysis of the influence of variables allows to conclude that:

for model configurations of the "thick stratum" group, the irradiation parameters {wavelength 1034 cm-1; two different modulation frequencies: 50 Hz and 200 Hz} are those which are sufficient to obtain an accurate blood glucose measurement desired, the analysis of the module (equivalent to the amplitude) of the signal detected at each of these frequencies being sufficient;

for model configurations of the "thin stratum" group, the irradiation parameters {wavelength 1034 cm-1; two different modulation frequencies: 50 Hz and 400 Hz} and analysis of the module (equivalent to the ampli-tude) of the signal detected at each of these frequencies is sufficient to obtain a blood glucose measurement with the desired precision.

We therefore understand that the process makes possible to reduce energy consumption for each irradiation while controlling the precision of the measurement, thanks to an adaptation of the irradiation case to the configuration model detected.

Figure 7A:
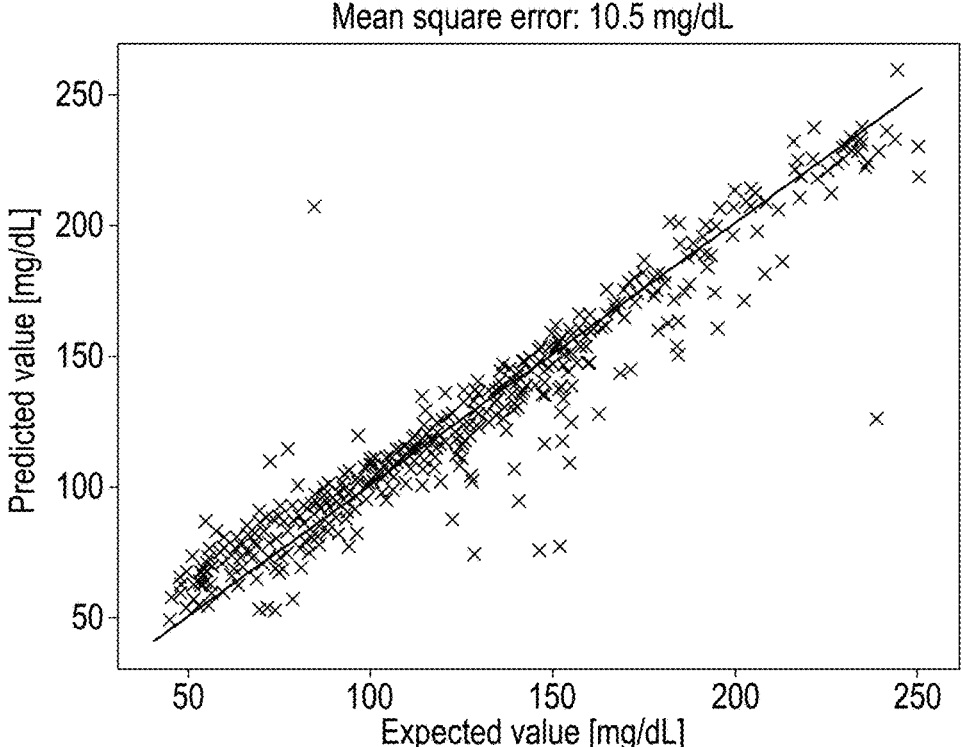
FIG. 7a shows the predicted blood glucose value by a first inverse model, trained on the first "thick stratum" group from signals detected following irradiation at six different modulations frequencies.
Figure 7B:
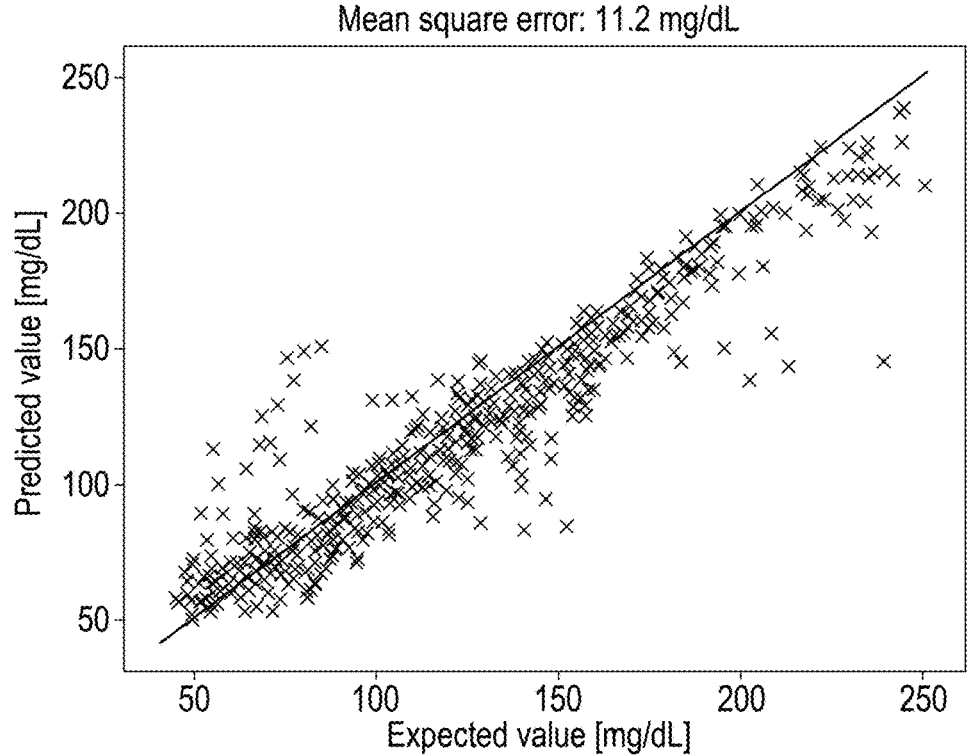
Figure 8A:
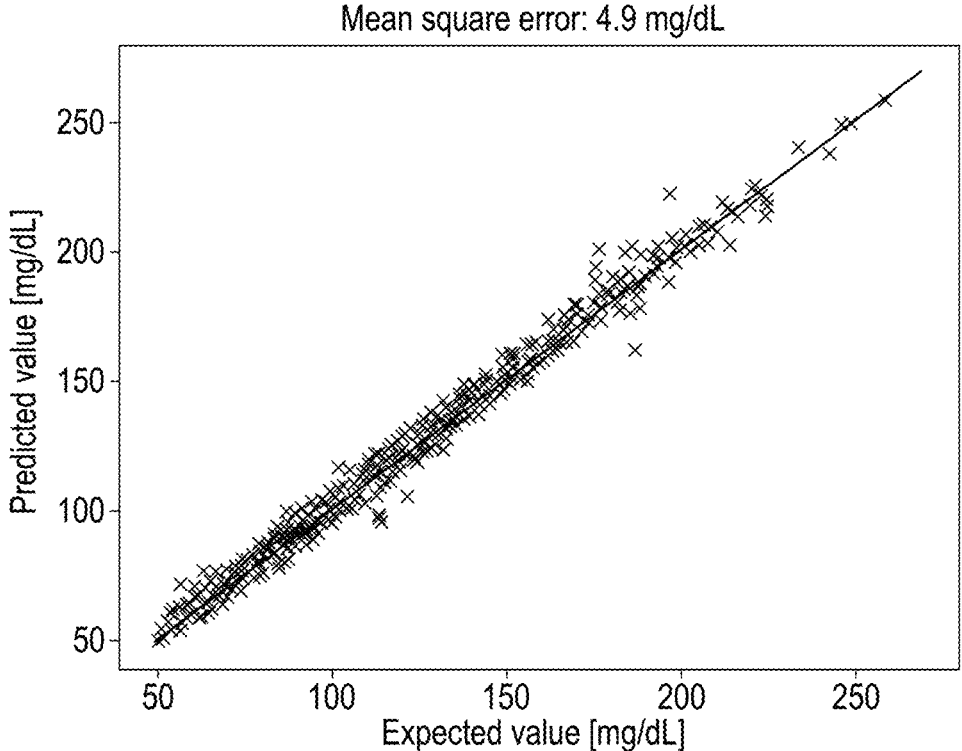
FIG. 8a shows the predicted blood glucose value by a third inverse model, trained on the second "thin stratum" group from the detected signals following irradiation at six different modulations frequencies.
Figure 8B:
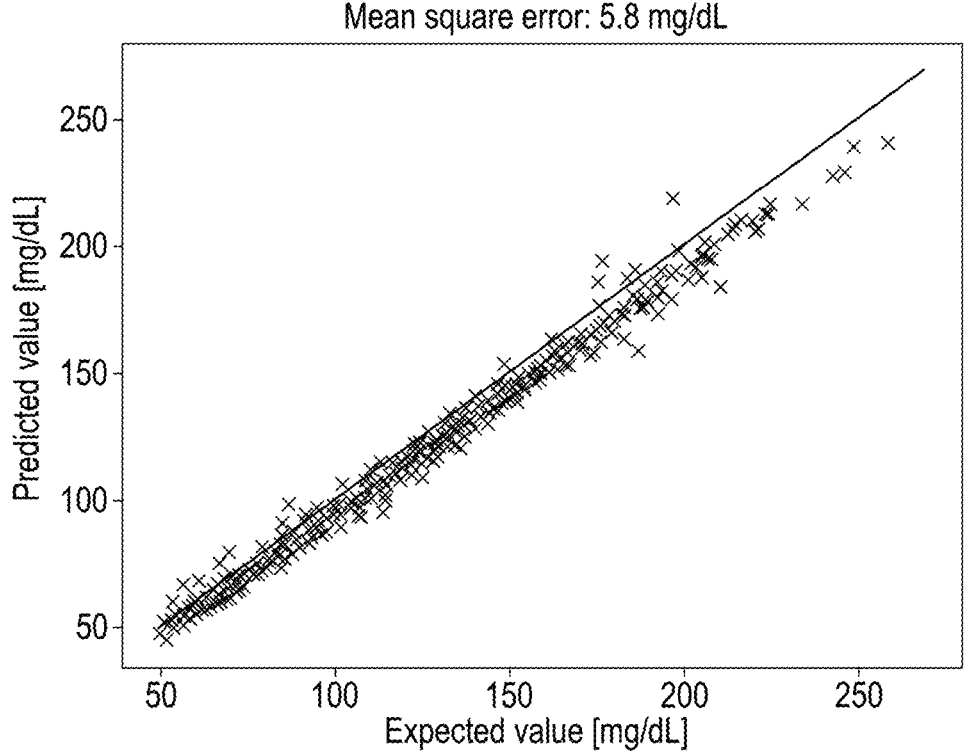
FIG. 8b represents the predicted blood sugar value by a fourth inverse model, trained on the second "thin stratum" group from the detected signals following irradiation depending on the two variables the most influential for this "thin stratum" group, identified in FIG. 6b.

We can convince ourselves of this by observing the measurement results obtained with complete irradiation, that is to say in this case following the six modulation frequen-cies envisaged (FIG. 7a for the "thick stratum" group, FIG. 8a for the "thin stratum" group), or with irradiation limited to the optimal irradiation case (FIG. 7b for the "thick stratum" group, FIG. 8b for the "thin stratum" group).

For the "thick stratum" group, the selection of two modu-lation frequencies only among the six possible (in this case 50 Hz and 200 Hz) and the analysis of only the amplitude (or equivalently the module) of the signal component detected at each of these frequencies led to:

a relative variation of the mean square error by 7%, with a reduction in consumption of one factor at least three, the mean square error going from 10.5 mg/dL to 11.2 mg/dL, therefore remaining well below the target threshold of 20 mg/dL considered the maximum acceptable RMSE in this case when selecting the variables of interest for the optimal irradiation case.

For the "thin stratum" group, the selection of only two modulation frequencies among the six possible (in this case 50 Hz and 400 Hz) and the analysis of only the amplitude (or equivalently the module) of the signal component detected at each of these frequencies led to:

a relative variation of the mean square error by 20%, with a reduction in consumption of one factor at least three, the mean square error going from 4.9 mg/dL to 5.8 mg/dL, therefore remaining well below the target threshold of 20 mg/dL considered to be the maximum acceptable RMSE in this case when selecting the variables of interest for the optimal irradiation case. Even if the relative variation of the mean square error is not negligible in this case, the absolute value of this mean square error therefore remains controlled during the selection of the optimal irradiation case.

On the other hand, in the absence of an association of model configurations for a particular irradiation case and to a particular inverse model, that is to say in the case where a single inverse model is trained for the whole model configurations of the two groups "thin stratum" and "thick stratum" and where the irradiation is made according to an irradiation case adapted to all of these model configurations of the two "thin stratum" and "thick stratum" groups, we see that the technical effect is not obtained.

Figure 6A:
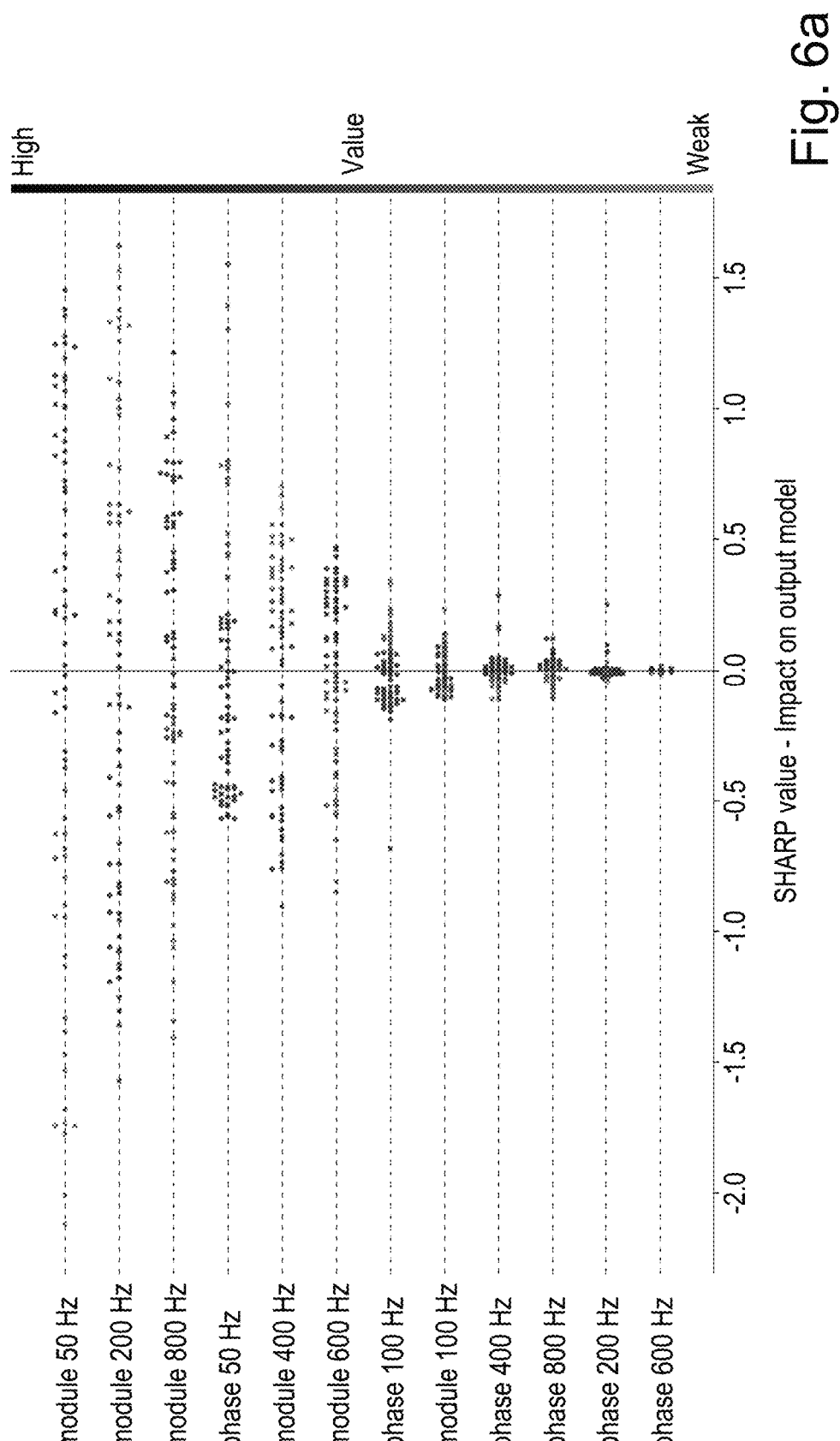
Figure 6B:
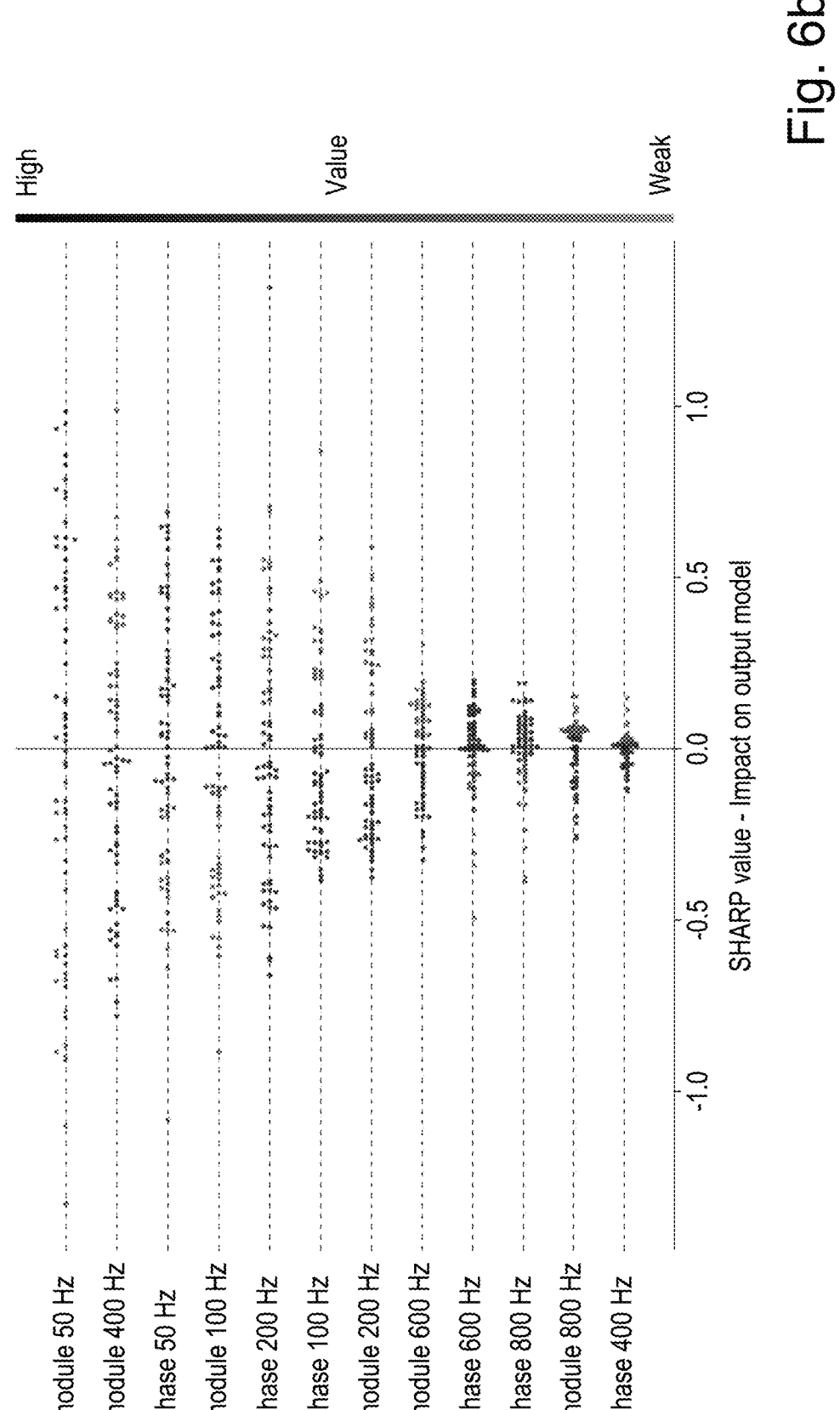
Figure 6C:
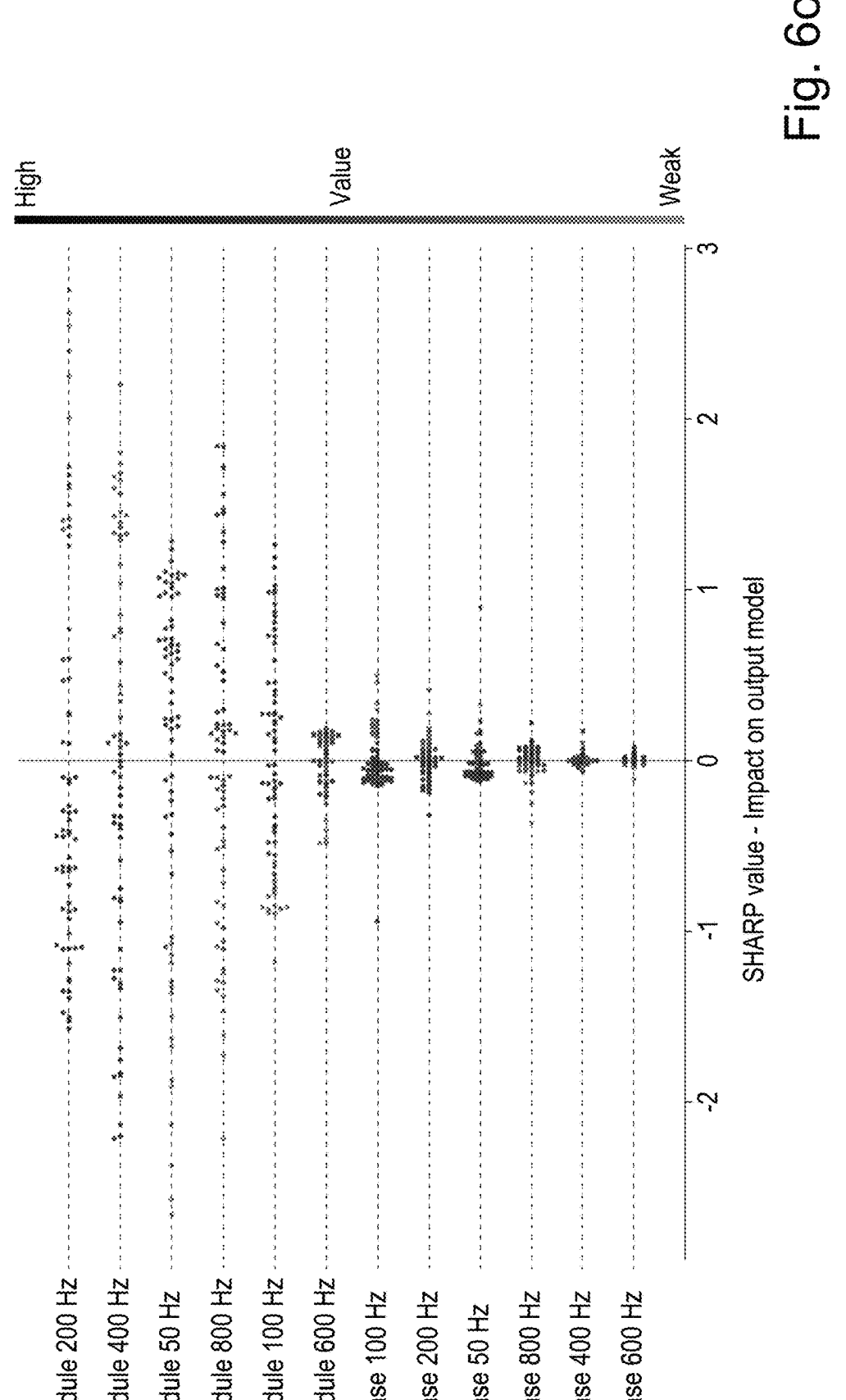

The optimal irradiation case selected for the whole of the two groups can be observed on the FIG. 6c, for which the irradiation parameters to be selected are {wavelength 1034 cm-1; two different modulations frequencies: 200 Hz and 400 Hz} and the analysis of the module (equivalently of the amplitude) of the signal detected at each of these frequencies that must be done.

Figure 9A:
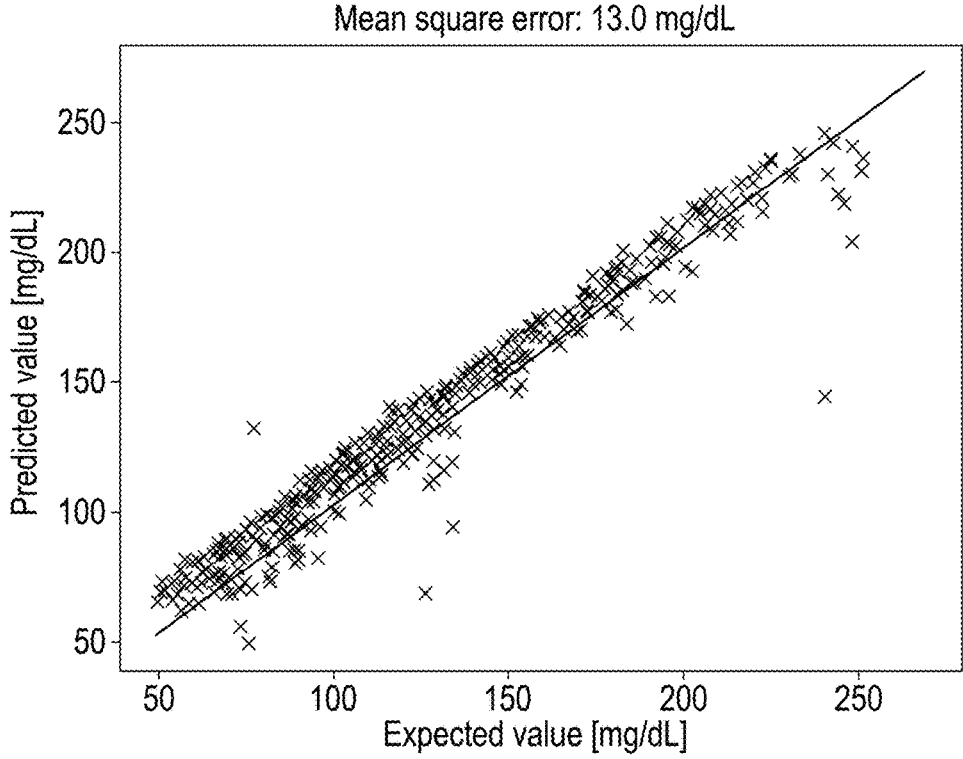
FIG. 9a shows the predicted blood glucose value by a fifth inverse model, trained on the whole of the two groups "thin stratum" and "thick stratum" from the signals detected following to irradiation at six different modulation frequencies.
Figure 9B:
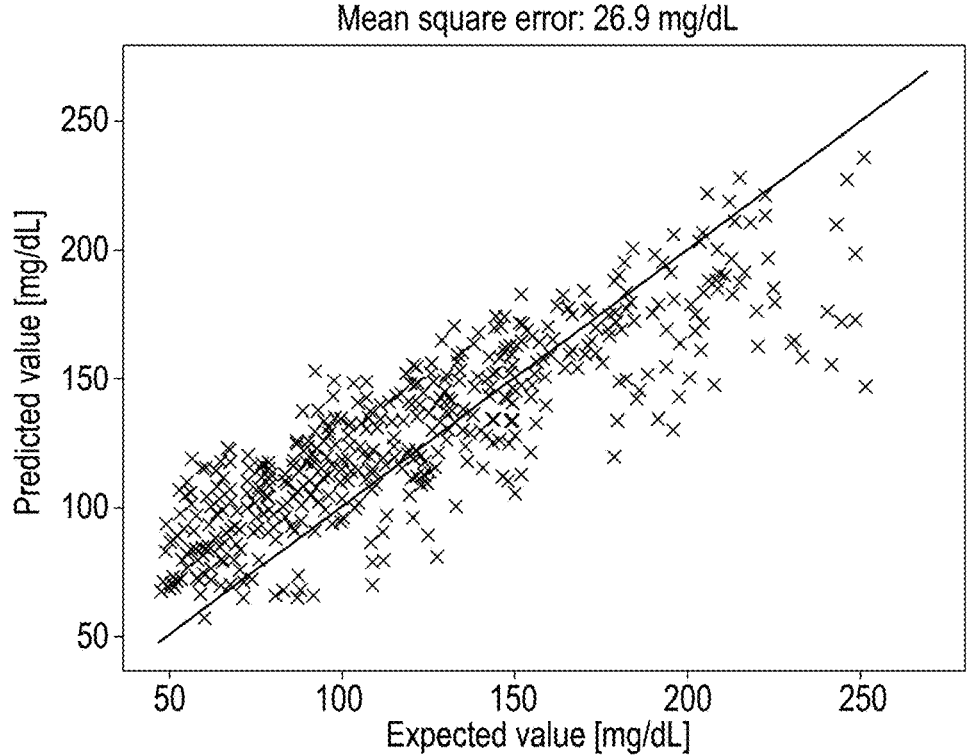
FIG. 9b shows the predicted blood glucose value by a sixth inverse model, trained on the whole of the two groups "thin stratum" and "thick stratum" from the signals detected following to irradiation according to the two most important variables influential for this set of two groups "thin stratum" and "thick stratum" identified on the FIG. 6c.

As can be observed in FIGS. 9a and 9b, the mean square deviation is multiplied by a factor three when we go from irradiation following six different modulation frequencies (RMSE=13.0 mg/dL) to irradiation following the two iden-tified modulation frequencies as the most influential (namely 200 Hz and 400 Hz) (RMSE=26.9 mg/dL), with analysis of only the amplitude of the signal detected at each of these frequencies. The threshold value for the RMSE, fixed for this example at 20 mg/dL, is also exceeded, indicating that other influencing variables must be taken into account to respect this threshold value.

The correspondence table can possibly include an optimal irradiation case for the whole groups, particularly with a view to initial irradiation. In the example above, we understand that it would have been necessary to include at least one additional modulation frequency, namely 50 Hz, to satisfy the criterion on the RMSE value for the initial irradiation. Consumption could then perhaps have been reduced, but only by a factor of two.

We therefore see in FIGS. 7a to 9b that the technical effect of reducing consumption at precision controlled measurement is obtained in particular by means of the correspondence table, which makes possible to segment the set of possible states of the target environment 2 in several categories and associate an optimal irradiation case for each of these categories.

In this case, the number of irradiation parameters (i.e. the two quantities carrying the most information) was selected to ensure that the RMSE remains less than 20 mg/dL even with irradiation that does not include all possibilities, and the precision is better than this threshold value at low blood sugar, according to usage in the field of blood glucose sensors. But it would be possible to select three, four or more of irradiation parameters among all possible for ensure an RMSE value lower than another threshold value, for example 15 mg/dL or 10 mg/dL or even 5 mg/dL.

The number of irradiation parameters selected results from a compromise between the available power for each irradiation and the acceptable RMSE.

The couples {CMk; I opt. k} or {category k of model configurations, Iopt.cat.k} are stored in a correspondence table in the memory of the non-invasive sensor 1, for example in a memory of the simulation module 15 and/or adaptation module 14.

The inverse models corresponding to each CMk model configuration or each category model configurations are also stored in the memory of the non-invasive sensor 1, for example in a memory of the simulation module 15 and/or of the adaptation module 14.

At this stage, the necessary elements for the implementation of the measurement method according to the invention are ready.

We already understand that thanks to the table correspondence, it is not necessary during a measure to establish a complete optical spectrum of the target for the state of the target being measured: automatic choice of the optimal irradiation case corresponding to the current model configuration, that is to say the values level 1 parameters best describing the target environment 2 for the current measurement, can be carried out from the correspondence table.

The measurement method according to the invention allows therefore to reduce the energy consumption of the sensor 1 compared to the processes of the prior art with an identical or even improved precision.

Method of Measuring the Parameter of Interest

The method of measuring the parameter of interest by means of the non-invasive sensor 1 based on the indirect photoacoustics detection is shown in FIG. 2. It includes the following steps:
a) Initialization:
We choose an initial model configuration of target environment 2 for the first irradiation based on predetermined criteria. For example, for FIG. 2, the Initial model configuration CMirrad is the model configuration CMk.

Different options can be used to this initialization.

In particular, in the case of measuring blood sugar interstitial from the database of the model configuration and/or a database from experimental measurements, we can determine a set of level 1 parameters and blood glucose average for a patient population or for a given patient. This set of average parameters corresponds to an initial model configuration CMk which has the greatest probability to be the most suitable for coming measurein the absence of any other information and particularly in the absence of a history measurement.

b) From the correspondence table, the processor of the adaptation module 14 determines the irradiation case Iopt.k associated with the initial model configuration, for example CMk.

c) First irradiation: We carry out a first irradiation of the target environment 2 with the light source(s) 11a depending on the irradiation parameters of the optimal irradiation case Iopt.k for the CMk model configuration.

d) PA detection:
We detect by means of the photoacoustic detection cell 12 the actual photoacoustic signal generated in response to irradiation. Where applicable, the signal processing module 13 receives and processes this real photoacoustic signal and transmits it after processing to the adaptation module 14.

e) Solving the inverse problem:
The processor of the adaptation module 14 implementing the inverse model(s) learned (and in particular at least that corresponding to the model configuration CMk) receives as input the real photoacoustic signal and the irradiation case Iopt.k and determines the model configuration of target environment 2 in progress, noted CMmes as well as the parameter of interest (as shown in FIG. 5).

f) Validation of the model configuration:
The adaptation module 14 compares the model configuration of target environment 2 in progress CMmes to the CMirrad model configuration used for irradiation (CMk model configuration from the initialization step for the first measurement, CMC model configuration possibly different for further measurement). There are two possible scenarios:

Case 1) If the model configuration of target environment 2 measured CMmes is identical to CMirrad model configuration which was used for irradiation, the irradiation parameters chosen were optimal for the physiological situation in progress (which we remind is not known to a priori and evolves over time), likewise that the inverse model used to determine the parameter of interest. Consequently, the parameter of interest determined in step f by the adaptation module 14 is the result of the measurement.

Case 2) If the model configuration of target environment 2 measured CMmes is different from the CMirrad model configuration, the adaptation module processor determined using the correspondence table a new model configuration CMℓ (ℓ/k) better suited to the CMmes model configuration estimated by the adaptation module 14. In particular, it is possible to choose CMℓ=CMmes. But other choices are possible, especially if we want to take into account the history of measurements over a longer period, taking into account at least two previously chosen model configurations. The processor of the adaptation module 14 searches then in the correspondence table the optimal irradiation case Iopt. $\ell$ for model configuration of target environment 2 CM$\ell$ and transmits the corresponding parameters to the irradiation device 11.

The target environment 2 then undergoes a new irradiation (subsequent irradiation) depending on the irradiation parameters of the irradiation case Iopt. $\ell$. Then steps d) of detection and, where applicable photoacoustic signal processing and e) resolution of the inverse problem are reiterated.

The method can comprise at most one step f) validation of the model configuration.

Alternatively, the method may also include a reiteration of step f) of validation of the model configuration.

The model configuration of target environment 2 in CMmes course may be different from model configuration CMirrad. Indeed, CMirrad was chosen either according to the initialization criteria (CMirrad is then the "average" model configuration, notably in the absence of measurement history on the patient. This is the case for the first irradiation);

either on the basis of the previous measurement (CMirrad is then the most suitable model configuration for the patient knowing the result of the measurement after the previous irradiation).

The validation of CMirrad is therefore carried out thanks to additional information acquired through irradiation in progress, namely the signal detected by the photoacoustic detection cell 12. If by chance, CMmes=CMirrad, it is not necessary to carry out a new irradiation and the value of the parameter of interest is although the most precise that could be obtained, but the validation step of the model configuration provided additional information, namely confirmation that the precision of the measurement is maximum for this case.

In the case, CMmes is different from CMirrad, the adaptation of the irradiation parameters and the configuration model increases the accuracy of the measurement at the cost of at least one additional irradiation but with energy consumption always under control, and thanks to the second validation step, to confirm that the precision of the measurement is maximum.

In the case where we authorize the reiteration of the step of validation (as shown in FIG. 2), we acquire at the output of the process the additional information that the measurement precision is maximum.

In general, in this case, the measurement result of the parameter of interest is obtained after the first irradiation or after two irradiations. However, to ensure that the process converges and/or limit consumption energy, we can foresee a limitation of the number of validation steps of the model configuration.

In all cases, we see that the choice of an irradiation case Ij based on the correspondence table allows to limit the number of modulation frequencies and wavelengths used for irradiation by retaining only the values carrying non-redundant information on the model configuration of physiological target environment 2 in progress and sufficient to obtain the desired and/or optimal measurement precision to limit the energy consumption of the sensor to a predetermined value.

For example, if the physiological situation corresponds with 3 layers each characterized by 2 concentrations (e.g. water and blood sugar), the resolution of the inverse problem is a problem with 2*3=6 unknowns. Knowledge of the amplitude and phase of each of the three components of the photoacoustic signal corresponding to modulation frequencies and well-chosen wavelengths should allow the resolution of the inverse problem with the desired precision. The difficulty lies in the optimal choice of these modulation frequencies and optimal wavelengths, which is solved using the correspondence table.

The consumption of sensor 1 is therefore limited or controlled.

Even in the case where two or three irradiations are necessary, each irradiation step requires limited power, less than that necessary for obtaining a complete absorption spectrum for each possible frequency modulation.

The model configuration validation step allows:

automatic recalibration of sensor 1 which ensures that the inverse model allowing to deduce a value of the parameter of interest of a photoacoustic signal detected is the most relevant inverse model for the current physiological situation, without a priori knowledge of this physiological situation the adjustment of the irradiation case, which ensures that the parameters used for subsequent irradiation are optimal in relation to the knowledge we have of the target environment and in particular that provided by the last photoacoustic signal detected.

Several embodiments can be considered to further optimize the process measurement according to the invention.

In particular, the artificial intelligence model of the simulation device 15 can be pre-trained on the database of simulated model configurations then re-trained on a database experimental model configuration, corresponding to real situations for a given patient or group of given patients, in order to ensure that the inverse model correctly predicts actual situations without this require having a set of exhaustive experimental data. Inverse learning models can include in this case a transfer learning stage ("transfer learning").

LIST OF REFERENCE SIGNS

1: non-invasive sensor based on indirect photoacoustic detection
11: irradiation device
11a: light source
11b: device for modulating the intensity of the light source 11a
11c: modulation frequency control device f mod of the intensity of the light source 11a
12: detection cell
13: signal processing module
14: adaptation module
15: simulation module

The invention claimed is:

1. A method of measuring a parameter of interest in a target environment by means of a non-invasive sensor based on photoacoustic detection or photothermal detection, wherein the method comprises:

a) providing a sensor, the sensor comprising:
   a light source,
   a device configured to control the irradiation parameters of the light source,
   a detection cell configured to detect an acoustic or thermal signal, a memory in which a correspondence table is stored, the correspondence table comprising model configurations each representative of a given state of a target environment and optimal irradiation cases each comprising a set of irradiation parameters, each model configuration being associated with an optimal irradiation case of the optimal irradiation cases, and an adaptation module configured to exchange information with the detection cell and the light source irradiation parameter control device, said adaptation module comprising a processor adapted to implement an inverse modeling algorithm configured to receive, as an input, an irradiation case comprising a set of irradiation parameters and an acoustic or thermal signal and configured to provide, as an output, a model configuration and a value of the parameter of interest;

b) selecting, by the adaptation module, an initial irradiation model configuration;

c) determining, by the adaptation module, the optimum irradiation case for the selected irradiation model configuration from the correspondence table as the irradiation case that allows the parameter of interest to be measured with a pre-determined accuracy and/or the quantity of measurement data allowing the lowest energy consumption;

d) irradiating, by the light source, the target environment according to the set of irradiation parameters of said optimal irradiation case;

e) detecting, by the detection cell, an acoustic or thermal signal generated in response to the irradiation by the light source;

f) implementing, by the processor of the adaptation module, the inverse modeling algorithm, receiving the acoustic or thermal signal detected by the detection cell and the optimal irradiation case used for irradiation, and returning a current model configuration and an estimated value of the parameter of interest;

g) evaluating, by the processor, the selected irradiation model configuration by comparison with the current model configuration, and only if the selected irradiation model configuration is different from the current model configuration: g1) receiving, by the adaptation module, the current model configuration, and returning, as an output, a new irradiation model configuration, and repeating steps c), d), e) and f), wherein the value of the parameter of interest measured by the sensor is the last value of the estimated parameter of interest.

2. The measurement method according to claim 1, further comprising repeating step g) after performing step f).

3. The measuring method according to claim 1, further comprising:

generating the correspondence table by a first processor and a database of model configurations comprising sets of respective model configurations, irradiation cases, and parameters of interest, and an acoustic or thermal signal detected by the detection cell associated with each set, wherein the correspondence table is stored in the memory of the non-invasive sensor.

4. The measurement method according to claim 3, wherein the first processor learns the inverse modeling algorithm from the database of model configurations and the inverse modeling algorithm is stored in the memory of the non-invasive sensor.

5. The measurement method according to claim 3, in which at least some of the acoustic or thermal signals detected by the sensor cell associated with the sets stored in the model configuration database are generated by a computerized simulation device.

6. A non-invasive sensor configured to measure a parameter of interest in a target environment based on photoacoustic or photothermal detection, the non-invasive sensor comprising:

a light source;

a device configured to control the irradiation parameters of the light source;

a detection cell configured to detect an acoustic or thermal signal;

a memory storing a correspondence table comprising model configurations each representative of a given state of the target environment and optimal irradiation cases each comprising a set of irradiation parameters, each model configuration being associated with one of the optimal irradiation cases; and an adaptation module adapted to exchange information with the detection cell and the light source for controlling the irradiation parameters of the light source, the adaptation module comprising a processor adapted to implement an inverse modeling algorithm configured to receive, as an input, an irradiation case comprising a set of irradiation parameters and an acoustic or thermal signal and configured to provide, as an output, a model configuration and a value of the parameter of interest, wherein the adaptation module is configured to:

i—select an initial irradiation model configuration, ii—determine an optimal irradiation case corresponding to an irradiation model configuration from the correspondence table, iii—transmit the determined optimal irradiation case to the light source irradiation parameter control device, iv—receive a signal detected by the detection cell, v—determine a current model configuration and an estimated value of the parameter of interest based on a detected photoacoustic or photothermal signal received and the determined optimal irradiation case, vi—evaluate the selected irradiation model configuration by comparison with the current model configuration, vii—only if the selected irradiation model configuration of a selected target stratified environment and the model configuration of a current target stratified environment are different, determine a new irradiation model configuration when the adaptation module receives the current model configuration, determine a new optimum irradiation case from a look-up table, corresponding to the new irradiation model configuration, and transmit the new optimum irradiation case to the irradiation parameter control device, so that the light source irradiates the target stratified environment according to the irradiation parameter set of the new optimum irradiation case, and the detection cell detects a new thermal or acoustic signal generated in response to this irradiation, and transmits it to the adaptation module configured to reiterate steps iv, v, vi and vii, and determine the value of the measured parameter of interest based on the last estimated value of the parameter of interest.

7. A non-transitory computer readable medium storing instructions which, when executed by a processor, cause the non-invasive sensor of claim 6 to perform steps i, ii, iii, iv, v, vi, and vii of claim 6.

* * * * *